(12) United States Patent
Takemura

(10) Patent No.: US 12,280,180 B2
(45) Date of Patent: Apr. 22, 2025

(54) MEDICAL DEVICE AND METHOD FOR PRODUCING MEDICAL DEVICE

(71) Applicant: TERUMO KABUSHIKI KAISHA, Tokyo (JP)

(72) Inventor: Naoto Takemura, Atsugi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 143 days.

(21) Appl. No.: 17/025,590

(22) Filed: Sep. 18, 2020

(65) Prior Publication Data

US 2021/0001012 A1 Jan. 7, 2021

Related U.S. Application Data

(63) Continuation of application No. PCT/JP2019/006869, filed on Feb. 22, 2019.

(30) Foreign Application Priority Data

Mar. 30, 2018 (JP) .................. 2018-067871

(51) Int. Cl.
| | | |
|---|---|---|
| A61L 29/08 | (2006.01) | |
| C08L 33/12 | (2006.01) | |
| C08L 83/06 | (2006.01) | |
| C08L 91/00 | (2006.01) | |

(52) U.S. Cl.
CPC .............. A61L 29/085 (2013.01); *C08L 33/12* (2013.01); *C08L 83/06* (2013.01); *C08L 91/00* (2013.01)

(58) Field of Classification Search
CPC ...... A61L 29/085; A61L 31/06; A61L 31/148; A61M 25/0045
See application file for complete search history.

(56) References Cited

U.S. PATENT DOCUMENTS

| | | | | |
|---|---|---|---|---|
| 5,531,715 | A | * | 7/1996 | Engelson .......... A61M 25/0045 604/525 |
| 2002/0168393 | A1 | * | 11/2002 | Sugimoto ............. A61L 31/148 424/422 |
| 2015/0152270 | A1 | * | 6/2015 | Aizenberg .............. A61L 31/06 508/106 |

FOREIGN PATENT DOCUMENTS

| | | |
|---|---|---|
| JP | S46-003627 B2 | 1/1971 |
| JP | S56-119262 A | 9/1981 |
| JP | S61-35870 B2 | 8/1986 |
| JP | S62-52796 B2 | 11/1987 |
| JP | H04-84970 A | 3/1992 |
| JP | H04-152952 A | 5/1992 |

(Continued)

OTHER PUBLICATIONS

International Searching Authority, "Written Opinion," issued in connection with International Patent Application No. PCT/JP2019/006869, dated Apr. 9, 2019.

(Continued)

*Primary Examiner* — Dah-Wei D. Yuan
*Assistant Examiner* — Andrew J Bowman
(74) *Attorney, Agent, or Firm* — Foley & Lardner LLP

(57) ABSTRACT

A medical device includes: a base material; and a coating on a surface of the base material. The coating includes a network structure including a thread portion and a network portion. The thread portion includes a combination of a silicone and a compound including a constituent unit of polymethoxyethyl acrylate (PMEA). The network portion includes a surface of the base material that is exposed from the thread portion.

11 Claims, 1 Drawing Sheet

(56) References Cited

FOREIGN PATENT DOCUMENTS

| JP | H07-178159 A  | 7/1995 |
| JP | 2011-067232 A | 4/2011 |
| JP | 2013-121430 A | 6/2013 |
| JP | 2017-025285 A | 2/2017 |
| JP | 2017-042533 A | 3/2017 |

OTHER PUBLICATIONS

Notice of Reasons for Refusal issued in connection with JP Appl. Ser. No. 2020-510454 dated Oct. 4, 2022.
International Searching Authority, "International Search Report," issued in connection with International Patent Application No. PCT/JP2019/006869, dated Apr. 9, 2019.

* cited by examiner

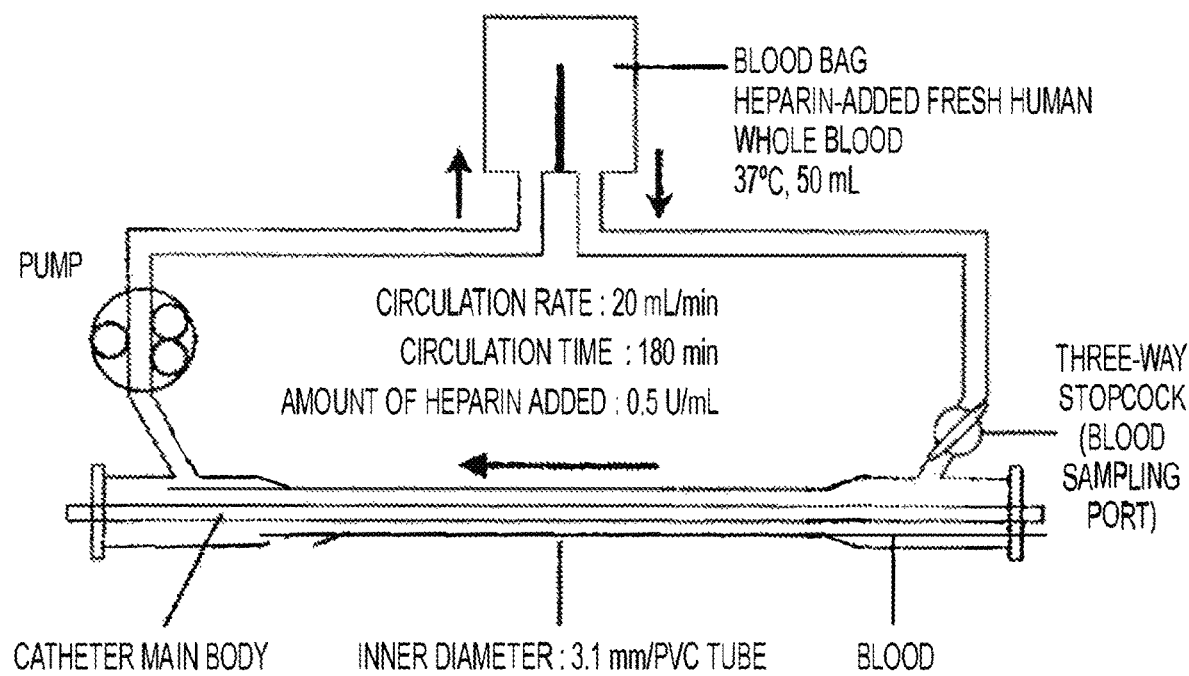

MEDICAL DEVICE AND METHOD FOR PRODUCING MEDICAL DEVICE

CROSS-REFERENCE TO RELATED APPLICATIONS

This is a bypass continuation of PCT Application No. PCT/JP2019/006869, filed on Feb. 22, 2019, which claims priority to Japanese Application No. 2018-067871, filed on Mar. 30, 2018. The contents of these applications are hereby incorporated by reference in their entireties.

BACKGROUND

The present disclosure relates to a medical device and a method for producing a medical device.

Medical devices that are inserted into the living body, such as catheters and indwelling needles, have been used for the purpose of fluid transfusion, blood transfusion, and the like. Regarding such medical devices, devices are known that have their surfaces treated with silicone in order to impart lubricating properties and to reduce friction at the time of performing puncture. For example, JP S61-35870 B discloses an injection needle having the surface treated with a composition that includes, as a main component, a reaction product between (i) a reaction product of an amino group-containing silane and an epoxy group-containing silane, and (ii) a polydiorganosiloxane containing a silanol group.

SUMMARY

The injection needle described in JP S61-35870 B has excellent puncture properties by having the surface reliably coated with silicone.

In a case in which the surface of a medical device (for example, an indwelling catheter) that is indwelled inside a blood vessel is coated with the composition described in JP S61-35870 B, excellent puncture properties are exhibited. However, there is a problem that, depending on the duration of indwelling (for example, 24 hours or longer), antithrombogenicity is not sufficient.

Therefore, certain embodiments of the present invention were developed in view of the circumstances described above, and it is an object of certain embodiments to provide a medical device that has excellent sliding properties (particularly, puncture properties) and exhibits excellent antithrombogenicity.

The inventors of the present invention conducted a thorough investigation in order to solve the above-described problems.

According to one embodiment, a medical device includes, on a surface of a base material, a coating that includes silicone and a compound including a constituent unit represented by the following Formula (I).

[Chemical Formula 1]

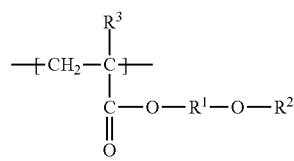

(I)

In Formula (I), $R^1$ represents an alkylene group having 1 to 4 carbon atoms, $R^2$ represents an alkyl group having 1 to 4 carbon atoms, and $R^3$ represents a hydrogen atom or a methyl group.

BRIEF DESCRIPTION OF DRAWINGS

The FIGURE is a schematic diagram illustrating a blood circulation experiment used in certain Examples.

DETAILED DESCRIPTION

Embodiments of the present invention will be described below. The present invention is not intended to be limited to only the following embodiments.

According to the present specification, the expression "X to Y" representing a range means "more than or equal to X and less than or equal to Y". Furthermore, unless particularly stated otherwise, operations and measurement of physical properties will be carried out under the conditions of room temperature (25±1° C.)/relative humidity of 40% to 50% RH.

<Medical Device>

One embodiment of the present invention is a medical device having, on a surface of a base material, a coating that includes silicone and a compound including a constituent unit represented by the following Formula (I).

[Chemical Formula 2]

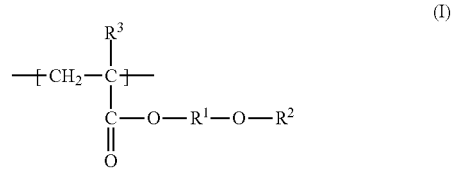

(I)

In Formula (I), $R^1$ represents an alkylene group having 1 to 4 carbon atoms, $R^2$ represents an alkyl group having 1 to 4 carbon atoms, and $R^3$ represents a hydrogen atom or a methyl group.

Because the medical device has, on the surface, a coating that includes silicone and a compound including a constituent unit represented by the above-described Formula (I), the medical device has excellent puncture properties and can exhibit excellent antithrombogenicity. The reason that such an effect can be achieved is not clearly understood; however, the reason is speculated as follows.

Because silicone having sliding properties and the above-described compound having antithrombogenicity form an appropriate size distribution state on the surface of the medical device, the medical device can comprise both of the properties. Furthermore, regarding antithrombogenicity, it is considered that the distribution of silicone (hydrophobic) and the above-described compound (hydrophilic) further enhances the properties.

Incidentally, the mechanism described above is merely a presumption, and the present invention is not intended to be limited to the presumption described above.

According to the present specification, the "surface" of a medical device refers to the surface of the material constituting the medical device and the surface portion of holes within the material constituting the medical device, which comes into contact with blood and the like when the medical device is used. For example, in a case in which the medical device is an indwelling catheter, the surface means the outer surface and/or inner surface.

(Silicone)

The coating according to the present embodiment includes silicone. The silicone is not particularly limited, and one or more kinds of biocompatible silicones can be selected and used as appropriate.

From the viewpoint of the stability of the form, it is preferable that the coating according to the present embodiment includes a cross-linked silicone as the silicone.

A cross-linked silicone is a silicone including three-dimensional bonds. Specific examples of the cross-linked silicone include (1) a reaction product between (i) a reaction product of an amino group-containing silane and an epoxy group-containing silane, and (ii) a polydiorganosiloxane containing a silanol group as described in JP S61-35870 B or JP S62-52796 B; and (2) a copolymer of an aminoalkylsiloxane and dimethylsiloxane as described in JP S46-3627 B.

Examples of the amino group-containing silane include γ-aminopropyltriethoxysilane, γ-aminopropylmethyldiethoxysilane, N-(β-aminoethyl)aminomethyltrimethoxysilane, γ-(β-aminoethyl)aminopropyltrimethoxysilane, γ-(N-(β-aminoethyl)amino)propylmethyldimethoxysilane, N-(β-aminoethyl)aminomethyltributoxysilane, and γ-(N-(β-(N-(β-aminoethyl)amino)ethyl)amino)propyltrimethoxysilane.

Examples of the epoxy group-containing silane include γ-glycidoxypropyltrimethoxysilane, γ-glycidoxypropylmethyldimethoxysilane, β-(3,4-epoxycyclohexyl)ethyltrimethoxysilane, β-(3,4-epoxycyclohexyl)ethylmethyldimethoxysilane, β-(3,4-epoxycyclohexyl)ethyltriethoxysilane, and β-(3,4-epoxycyclohexyl)ethylmethyldiethoxysilane.

The polydiorganosiloxane containing a silanol group has at least one silanol group in one molecule. The viscosity of the polydiorganosiloxane containing a silanol group is 0.00002 to 1 m$^2$/s, and preferably 0.0001 to 0.1 m$^2$/s, at 25° C. When the viscosity is 0.00002 m$^2$/s or higher, sufficient puncture properties can be obtained. When the viscosity is 1 m$^2$/s or lower, handling before curing is made easier. Examples of the organic group to be bonded to a silicon atom of the silanol group include an alkyl group such as a methyl group, a phenyl group, and a vinyl group. From the viewpoint of the ease of synthesis of the polydiorganosiloxane, the organic group is preferably a methyl group or a phenyl group, and more preferably a methyl group. Specific examples of the polydiorganosiloxane containing a silanol group include a polydimethylsiloxane having one terminal blocked with a silanol group and the other terminal blocked with a trimethylsilyl group, a polydimethylsiloxane having both terminals blocked with a silanol group, and a polymethylphenylsiloxane having both terminals blocked with a silanol group.

A reaction product of an amino group-containing silane and an epoxy group-containing silane can be obtained by heating and reacting the amino group-containing silane and the epoxy group-containing silane with stirring.

The reaction ratio of the amino group-containing silane and the epoxy group-containing silane is 0.5 to 3.0 mol, and preferably 0.75 to 1.5 mol, of the epoxy group-containing silane with respect to 1 mol of the amino group-containing silane.

A reaction product between a reaction product of an amino group-containing silane and an epoxy group-containing silane (component A), and a polydiorganosiloxane containing a silanol group (component B), can be obtained by reacting, while performing heating, the component A and component B using a solvent as necessary. The mixing ratio of the component A and component B is such that the proportion of the component A is 0.1% to 10% by mass, and the proportion of the component B is 90% to 99.9% by mass, with respect to the sum of the component A and component B. The mixing ratio is preferably such that the proportion of the component A is 1% to 5% by mass, and the proportion of the component B is 95% to 99% by mass.

Furthermore, a commercially available product can be used as the cross-linked silicone. Examples of a commercially available product that can be used include MDX4-4159 (manufactured by The Dow Chemical Company).

According to an embodiment, the coating according to the present embodiment can further include a silicone oil in addition to the cross-linked silicone. Thereby, the puncture properties can be further enhanced.

Examples of the silicone oil include dimethyl silicone oil, methyl phenyl silicone oil, methyl hydrogen silicone oil, amino-modified silicone oil, epoxy-modified silicone oil, carboxy-modified silicone oil, and fluorine-modified silicone oil. The silicone oil is preferably at least one of dimethyl silicone oil, methyl phenyl silicone oil, and methyl hydrogen silicone oil, and more preferably dimethyl silicone oil.

Furthermore, a commercially available product can be used as the silicone oil. Regarding a commercially available product that can be used, SH-200, SH510, SH550, SH710 (manufactured by Dow Corning Toray Co., Ltd.), KF-96, KF-96H, KF-965, KF-968, KF-50, KF-53, KF-54 (manufactured by Shin-Etsu Chemical Co., Ltd.), TSF451, TSF431, TSF433, TSF4300 (manufactured by Momentive Performance Materials Japan LLC), WACKER (registered trademark) SILICONE FLUID AK, AKF, AKC, AR (manufactured by Wacker Asahikasei Silicone Co., Ltd.), and the like can be used.

According to an embodiment, the coating according to the present embodiment can have a structure in which a lower layer includes the above-described compound and a cross-linked silicone, and an upper layer includes a silicone oil.

(Compound Including Constituent Unit Represented by Formula (I))

The coating according to the present embodiment includes a compound including a constituent unit represented by the following Formula (I).

[Chemical Formula 3]

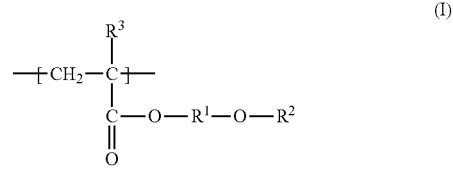

(I)

In the above-described Formula (I), R$^1$ represents an alkylene group having 1 to 4 carbon atoms, R$^2$ represents an alkyl group having 1 to 4 carbon atoms, and R$^3$ represents a hydrogen atom or a methyl group.

In the above-described Formula (I), R$^1$ represents a cyclic, linear, or branched alkylene group having 1 to 4 carbon atoms, and is preferably a linear or branched alkylene group having 1 to 4 carbon atoms. Specific examples include a methylene group, an ethylene group, a trimethylene group, a propylene group, a cyclopropylene group, a tetramethylene group, and a cyclobutylene group. Among these, when the effect of enhancing antithrombogenicity is considered, the alkylene group is preferably a linear or branched alkylene group having 1 to 3 carbon atoms, and particularly preferably a methylene group or an ethylene group.

In the above-described Formula (I), $R^2$ represents a cyclic, linear, or branched alkyl group having 1 to 4 carbon atoms, and is preferably a linear or branched alkyl group having 1 to 4 carbon atoms. Specific examples include a methyl group, an ethyl group, a propyl group, an isopropyl group, an n-butyl group, a sec-butyl group, a t-butyl group, a cyclopropyl group, and a cyclobutyl group. Among these, when the effect of enhancing antithrombogenicity is considered, the alkyl group is preferably a linear or branched alkyl group having 1 to 3 carbon atoms, more preferably a methyl group or an ethyl group, and particularly preferably a methyl group.

In the above-described Formula (I), $R^3$ represents a hydrogen atom or a methyl group, and is preferably a hydrogen atom.

The compound including a constituent unit represented by Formula (I) may further have another constituent unit. That is, the compound including a constituent unit represented by Formula (I) may be a copolymer including the constituent unit represented by the above-described Formula (I) and the other constituent unit. The structure of this "other constituent unit" is not particularly limited as long as the intended effects of the present invention are obtained. However, for example, it is preferable that the structure is a structure derived from the "other monomer" that will be described in detail below. In a case in which the compound including a constituent unit represented by Formula (I) is a copolymer, the structure thereof is also not particularly limited, and the compound may be any one of a random copolymer, an alternating copolymer, a periodic copolymer, and a block copolymer.

The compound including a constituent unit represented by Formula (I) is preferably a polymer comprising a constituent unit represented by the above-described Formula (I), and is more preferably a homopolymer derived from one kind of monomer, from the viewpoint of obtaining excellent antithrombogenicity and biocompatibility. Specific examples of such a polymer suitably include poly-2-methoxyethyl (meth)acrylate (polymethoxyethyl (meth)acrylate), polymethoxymethyl (meth)acrylate, polyethoxymethyl (meth)acrylate, polyethoxyethyl (meth)acrylate, polybutoxymethyl (meth)acrylate, and polybutoxyethyl (meth)acrylate. From the viewpoint of the solubility in a mixed solvent of water and an alcohol, polymethoxyethyl acrylate (also referred to as "poly-2-methoxyethyl acrylate" or "PMEA") is more preferred. In the present specification, the term "(meth)acrylate" means "acrylate and/or methacrylate".

The weight average molecular weight of the compound including the constituent unit represented by Formula (I) is, for example, 10000 to 2000000, and preferably 50000 to 1000000. Regarding the weight average molecular weight, a value measured by Gel Permeation Chromatography (GPC) using polystyrene as a reference material and tetrahydrofuran (THF) as a mobile phase is employed.

The method for producing the compound including a constituent unit represented by Formula (I) is not particularly limited. For example, the compound can be produced by polymerizing a monomer represented by the following Formula (II):

[Chemical Formula 4]

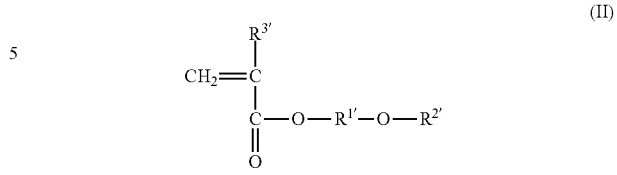

In Formula (II), because substituents $R^{1'}$, $R^{2'}$, and $R^{3'}$ have similar definitions as $R^1$, $R^2$, and $R^3$ in Formula (I), respectively, further description will not be repeated here.

Specific examples of the monomer represented by Formula (II) include methoxymethyl acrylate, methoxyethyl acrylate (MEA), methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, methoxymethyl methacrylate, methoxyethyl methacrylate, methoxypropyl methacrylate, methoxybutyl methacrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate, and butoxybutyl methacrylate. Among these, methoxymethyl acrylate, methoxyethyl acrylate (MEA), ethoxymethyl acrylate, ethoxyethyl acrylate, methoxymethyl methacrylate, methoxyethyl methacrylate, ethoxymethyl methacrylate, and ethoxyethyl methacrylate are preferred, and furthermore, from the viewpoint of saying that the compound is readily available, methoxyethyl (meth)acrylate is more preferred. Furthermore, these monomers can be used singly, or two or more kinds thereof can be used as a mixture.

Furthermore, in addition to the monomer represented by Formula (II), another monomer capable of copolymerizing with the monomer represented by Formula (II) (hereinafter, also simply referred to as "other monomer") may also be used. Examples of the other monomer capable of copolymerizing with the monomer represented by Formula (II) include acrylamide, N,N-dimethylacrylamide, N,N-diethylacrylamide, aminomethyl acrylate, aminoethyl acrylate, aminoisopropyl acrylate, diaminomethyl acrylate, diaminoethyl acrylate, diaminobutyl acrylate, methacrylamide, N,N-dimethylmethacrylamide, N,N-diethylmethacrylamide, aminomethyl methacrylate, aminoethyl methacrylate, diaminomethyl methacrylate, diaminoethyl methacrylate, methyl acrylate, ethyl acrylate, isopropyl acrylate, butyl acrylate, 2-ethylhexyl acrylate, methyl methacrylate, ethyl methacrylate, butyl methacrylate, hexyl acrylate, hexyl methacrylate, ethylene, and propylene.

The method for producing the compound including the constituent unit represented by Formula (I) is not particularly limited. For example, it is preferable that a solution obtained by dissolving a monomer represented by Formula (II) in a polymerizing solvent is mixed with a polymerization initiator solution that has been prepared separately, thereby a polymerization reaction solution is prepared, and a polymerization reaction is carried out.

The polymerizing solvent is not particularly limited as long as it can dissolve the monomer represented by Formula (II). For example, a polymerizing solvent including methanol as a main component is preferred. Meanwhile, the expression "as a main component" implies that in the entire solvent used for a methanol solution, the proportion of methanol is 95% by mass or more, and preferably 99% by mass or more (upper limit 100% by mass). Regarding the polymerizing solvent other than methanol included in the "methanol solution", for example, one kind or two or more kinds selected from water; alcohols such as ethanol, isopropanol, n-propanol, n-butanol, isobutanol, sec-butanol, t-butanol, ethylene glycol, diethylene glycol, propylene glycol, and dipropylene glycol; organic solvents such as chloroform, tetrahydrofuran, acetone, dioxane, and benzene may be mentioned. However, the polymerizing solvent is not limited to these. Furthermore, the concentration of the monomer represented by Formula (II) that is included in the polymerizing solvent is not particularly limited. For example, by setting the concentration to be relatively high, the weight average molecular weight of the resulting compound including the constituent unit represented by Formula (I) can be made larger. Therefore, from the viewpoint of adjusting the weight average molecular weight of the compound including a constituent unit represented by Formula (I), the concentration of the monomer represented by Formula (II) in the polymerizing solvent is preferably 25% by mass or more, more preferably 30% by mass or more, and particularly preferably 50% by mass or more. Furthermore, the upper limit of the monomer concentration is not particularly limited. For example, the monomer concentration is equal to or less than the saturation concentration, and the monomer concentration is, for example, 90% by mass or less, and preferably 70% by mass or less.

Furthermore, the polymerizing solvent to which the monomer represented by Formula (II) has been added may be subjected to a degassing treatment at a temperature of about 30° C. to 70° C. before the addition of a polymerization initiator. Regarding the degassing treatment, for example, bubbling may be performed for about 0.5 to 5 hours with an inert gas such as nitrogen gas or argon gas.

Furthermore, the polymerization initiator to be used at the time of producing the compound including a constituent unit represented by Formula (I) is not particularly limited, and any known polymerization initiator can be used. Preferably, from the viewpoint of having excellent polymerization stability, a radical polymerization initiator is used, and specific examples include persulfates such as potassium persulfate (KPS), sodium persulfate, and ammonium persulfate; peroxides such as hydrogen peroxide, t-butyl peroxide, and methyl ethyl ketone peroxide; azobisisobutyronitrile (AIBN), 2,2'-azobis(4-methoxy-2,4-dimethylvaleronitrile), 2,2'-azobis(2,4-dimethylvaleronitrile), 2,2'-azobis [2-(2-imidazolin-2-yl) propane] dihydrochloride, 2,2'-azobis [2-(2-imidazolin-2-yl) propane] disulfate dihydrate, 2,2'-azobis(2-methylpropionamidine) dihydrochloride, 2,2'-azobis [N-(2-carboxyethyl)-2-methylpropionamidine] hydrate, 3-hydroxy-1,1-dimethylbutyl peroxyneodecanoate, α-cumyl peroxyneodecanoate, 1,1,3,3-tetrabutyl peroxyneodecanoate, t-butyl peroxyneodecanoate, t-butyl peroxyneoheptanoate, t-butyl peroxypivalate, t-amyl peroxyneodecanoate, t-amyl peroxypivalate, di(2-ethylhexyl) peroxydicarbonate, di(s-butyl) peroxydicarbonate, and azo compounds such as azobiscyanovaleric acid. Furthermore, for example, the above-described radical polymerization initiator may also be used in combination with a reducing agent such as sodium sulfite, sodium hydrogen sulfite, or ascorbic acid, as a redox-based initiator. The mixing amount of the polymerization initiator is preferably 0.005 to 2 parts by mass, and more preferably 0.01 to 2 parts by mass, with respect to 100 parts by mass of a monomer represented by Formula (II) (in the case of using a plurality of kinds of monomers, all of the monomers). When such a mixing amount of the polymerization initiator is used, a compound including a constituent unit represented by Formula (I) and having a desired weight average molecular weight can be produced more efficiently.

Furthermore, the above-described polymerization initiator may be mixed directly with the monomer represented by Formula (II) and the polymerizing solvent. However, it is also acceptable that the polymerization initiator may be mixed, in the form of a solution of being dissolved in advance in another solvent (initiator solution), directly with the monomer represented by Formula (II) and the polymerizing solvent. In the case of the latter, the other solvent is not particularly limited as long as it can dissolve the polymerization initiator. For example, solvents similar to the polymerizing solvents described above may be mentioned as examples. Furthermore, in all cases, a polymerization initiator, a monomer represented by Formula (II), and a solvent (a solvent obtained by combining a polymerizing solvent and another solvent (solvent of an initiator solution) used as necessary) are combined, and thereby the above-described "polymerization reaction solution" is formed. The concentration of the monomer represented by Formula (II) in this polymerization reaction solution is not particularly limited. For example, from the viewpoint of adjusting the weight average molecular weight of the compound including a constituent unit represented by Formula (I), the concentration of the monomer represented by Formula (II) in the polymerization reaction solution is preferably 25% by mass or more, more preferably 30% by mass or more, and particularly preferably 50% by mass or more. Furthermore, the upper limit is not particularly limited. For example, the concentration of the monomer represented by Formula (II) is equal to or less than the saturation concentration, and the concentration is, for example, 90% by mass or less, and preferably 70% by mass or less. Furthermore, the other solvent may be identical to or different from the polymerizing solvent. However, because the ease of control of polymerization and the like are considered, it is preferable that the other solvent is the same solvent as the polymerizing solvent.

According to certain embodiments of the present invention, by heating the polymerization reaction solution including the monomer represented by Formula (II), an alkoxyalkyl (meth)acrylate or an alkoxyalkyl (meth)acrylate and another monomer can be (co) polymerized. Regarding the polymerization method, for example, in addition to the above-described radical polymerization, a known polymerization method such as anionic polymerization or cationic polymerization can be employed, and preferably, radical polymerization by which production is made easy is used.

The polymerization conditions are not particularly limited as long as they are conditions in which the monomer represented by Formula (II) can be polymerized. Specifically, the polymerization temperature is preferably 30° C. to 60° C., and more preferably 40° C. to 55° C. Furthermore, the polymerization time is preferably 1 to 24 hours, and preferably 3 to 12 hours. Under such conditions, a polymer having a high molecular weight such as described above can be produced more efficiently. Furthermore, gelation can be effectively suppressed or prevented in the polymerization step, and also, high production efficiency can be achieved.

Furthermore, if necessary, a chain transfer agent, a polymerization rate adjusting agent, a surfactant, and other additives may also be appropriately used at the time of polymerization.

The atmosphere in which the polymerization reaction is carried out is not particularly limited, and the reaction can also be carried out under an air atmosphere, under an inert gas atmosphere such as nitrogen gas or argon gas, or the like. Furthermore, during the polymerization reaction, the reaction solution may be stirred.

The polymer after polymerization can be purified by a general purification method such as a reprecipitation method, a dialysis method, an ultrafiltration method, or an extraction method. For the reason that a (co) polymer appropriate for the preparation of a colloid solution is obtained, among the above-described methods, it is preferable to perform purification according to a reprecipitation method. At this time, regarding a poor solvent that is used for performing reprecipitation, it is preferable to use ethanol.

The polymer (that is, the compound including a constituent unit represented by Formula (I)) after purification can be dried according to any arbitrary method such as freeze-drying, drying under reduced pressure, spray drying, or heat drying. For example, from the viewpoint that the influence exerted on the physical properties of the polymer is small, freeze-drying or drying under reduced pressure is preferred.

The compound including a constituent unit represented by the above-described Formula (I) can be obtained by the above-mentioned production method.

(Coating)

The medical device according to certain embodiments of the present disclosure has, on the surface, a coating that includes silicone and a compound including a constituent unit represented by the above-described Formula (I). According to the present specification, the term "coating" means that at least a portion of the surface of a medical device is covered with silicone and a compound including a constituent unit represented by the above-described Formula (I). That is, regarding the surface of the medical device of the present embodiment, a portion of the surface may be covered, or the entire surface may be covered, with silicone and a compound including a constituent unit represented by Formula (I).

According to the present specification, the expression "the surface is covered" includes a state in which a structure that includes silicone and a compound including a constituent unit represented by Formula (I) is formed on the surface of a medical device. Examples of this structure include a network structure and a sea-island structure. Above all, from the viewpoint that the effects of the present invention are further exhibited, it is preferable that the coating has a network structure. The structure formed on the surface of a medical device can be confirmed by observing the surface with a laser microscope (for example, the objective lens 150 times).

A network structure is a structure extending in a network form and is composed of a thread portion and a network portion. In the network structure, the thread portion includes silicone and a compound including a constituent unit represented by Formula (I). At the network portion, the surface of the base material may be exposed without being substantially covered.

Furthermore, the coating according to the present embodiment may be formed from two or more kinds of structures. For example, the coating may be formed from a network structure portion and a covering portion that covers this network structure.

The coating according to the present embodiment can further include a component other than the silicone and the compound including a constituent unit represented by Formula (I) (other component). Regarding the other component, a drug having pharmacological action with sustained release properties, for example, an antibacterial agent or an antithrombotic agent, may be mentioned.

(Medical Device)

Regarding the medical device of the present embodiment, a device that is used in contact with body fluid, blood, or the like may be mentioned. As mentioned above, because the surface of a medical device has a coating that includes silicone and a compound including a constituent unit represented by the above-described Formula (I), the medical device has excellent sliding properties and can exhibit excellent antithrombogenicity. Therefore, the medical device of the present embodiment may be used for any use application as long as sliding properties and/or antithrombogenicity is required for the use application. Examples thereof include a catheter, a sheath, a cannula, a needle, a three-way stopcock, and a guide wire. Furthermore, other examples include a blood circuit, an artificial dialyzer, an artificial (auxiliary) heart, an artificial lung, an indwelling needle, an artificial kidney, and a stent. In the case of a medical device that is inserted or indwelled in a body cavity such as a blood vessel, this device can have the above-described structure on at least a portion of the outer surface, in order to enhance the sliding properties when the device comes into contact with the body cavity. In the case of a medical device having another device inserted into the internal space thereof, such as a catheter or a sheath, the medical device can have the above-described structure on at least a portion of the surface of the internal space, in order to enhance the sliding properties when the other device is inserted. Particularly, the medical device of the present embodiment is suitably used as an indwelling catheter because the sliding properties, particularly puncture properties, and antithrombogenicity can be obtained in a well-balanced manner.

<Method for Producing Medical Device>

Another embodiment of the present invention is a method for producing a medical device, the method including coating a mixed solution that includes silicone and a compound including a constituent unit represented by the following Formula (I) on a base material.

[Chemical Formula 5]

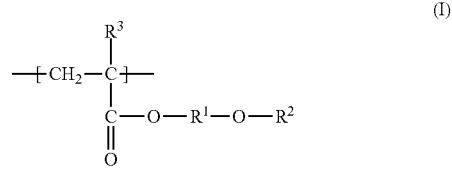

(I)

In Formula (I), $R^1$ represents an alkylene group having 1 to 4 carbon atoms, $R^2$ represents an alkyl group having 1 to 4 carbon atoms, and $R^3$ represents a hydrogen atom or a methyl group.

(Mixed Solution)

Because the silicone and the compound including a constituent unit represented by the above-described Formula (I) are similar to those of the embodiment of the medical device as described above, further description will not be repeated.

The method for preparing the mixed solution is not particularly limited, and for example, the mixed solution can be produced by dissolving silicone and the compound including a constituent unit represented by Formula (I) in a solvent. The solvent is not particularly limited as long as it can dissolve silicone and the compound including a constituent unit represented by Formula (I). For example, in the case of using a cross-linked silicone as the silicone and polymethoxyethyl acrylate as the compound including a constituent unit represented by Formula (I), dichloropentafluoropropane, methylene chloride, hydrochlorofluoroolefin, trans-1,2-dichloroethylene, chloroform, or the like can be used as the solvent.

The concentration of silicone in the mixed solution is not particularly limited. For example, the concentration is, for example, 0.1 to 20 v/v %, and preferably 1 to 10 v/v %. In a case in which two or more kinds of silicones are used, the concentration of the silicones is the total concentration of those silicones.

The concentration of the compound including a constituent unit represented by Formula (I) in the mixed solution is not particularly limited. However, the concentration is, for example, 0.05 to 2.0 v/v %, and preferably 0.1 to 0.5 v/v %.

(Base Material)

The material for the base material of the medical device is not particularly limited, and examples include, for example, various polymer materials, including polyolefins such as polyethylene, polypropylene, and an ethylene-α-olefin copolymer, and modified polyolefins; polyamides; polyimides; polyurethanes; polyesters such as polyethylene terephthalate (PET), polybutylene terephthalate (PBT), polycyclohexane terephthalate, and polyethylene-2,6-naphthalate; polyvinyl chloride; polyvinylidene chloride (PVDC); and fluororesins such as polytetrafluoroethylene (PTFE), and an ethylene-tetrafluoroethylene copolymer (ETFE), metals, ceramics, carbon, and composite materials of these. The above-described polymer materials may be materials that have been subjected to a stretching treatment (for example, ePTFE).

The shape of the base material is appropriately selected according to the use application or the like of the medical device, and for example, a shape such as a tube shape, a sheet shape, or a rod shape can be adopted. The form of the base material is not limited to a molded body using a material such as described above alone, and a blend molded product, an alloyed molded product, a multilayered molded product, or the like can also be used. The base material may be single-layered, or may be laminated. At this time, in a case in which the base material is laminated, the base materials of the respective layers may be identical or may be different.

(Coating)

The method of coating the base material with the mixed solution is not particularly limited, and conventionally known methods such as an application or printing method, an immersion method (dipping method, dip coating method), a spraying method (spray method), a spin coating method, and a mixed solution-impregnated sponge coating method, can be used.

According to a preferred embodiment of the present aspect, the method of coating the base material with the mixed solution is an immersion method (dipping method). The immersion temperature is not particularly limited, and for example, the immersion temperature is 10° C. to 50° C., and preferably 15° C. to 40° C. The immersion time is not particularly limited, and for example, the immersion time is 10 seconds to 30 minutes.

Incidentally, in a case in which a coating is formed on a slender and narrow inner surface of a catheter, a guide wire, an injection needle, or the like, the base material may be immersed in the mixed solution, and thereby the inside of the system may be degassed by lowering the pressure. Because degassing is achieved by lowering the pressure, the solution can be rapidly immersed into the slender and narrow inner surface, and the formation of a coating can be accelerated.

After the base material is immersed in the mixed solution, the base material is taken out and is subjected to a drying treatment. The rate at which the base material is pulled up is not particularly limited and is, for example, 1 to 50 mm/sec. The drying conditions (temperature, time, and the like) are not particularly limited as long as they are conditions in which a coating can be formed on the surface of the base material. Specifically, the drying temperature is preferably 20° C. to 150° C. The drying time is preferably 20 minutes to 2 hours, and preferably 30 minutes to 1 hour.

The pressure conditions at the time of drying are also not limited, and drying may be carried out at normal pressure (atmospheric pressure) and also may be carried out under pressure or under reduced pressure.

Regarding the drying unit (apparatus), for example, an oven, a reduced pressure dryer, and the like can be utilized. For example, in the case of natural drying, a drying unit (apparatus) in particular is unnecessary.

Through the above-described method, a medical device having, on the surface, a coating that includes silicone and a compound including a constituent unit represented by Formula (I) can be produced.

The coating may be formed from two or more kinds of structures as described above. For example, in a case in which the coating is formed from a network structure portion and a covering portion that covers this network structure, a coating formed from two kinds of structures can be obtained by coating a base material with a mixed solution including a cross-linked silicone and PMEA, forming a network structure on the surface of the base material, and then further coating the surface with a solution including a silicone oil.

(Other Steps)

The base material having a coating formed on the surface by the above-described method can be directly used as a medical device. However, it is also acceptable to wash the base material having a coating formed thereon.

The washing method is not particularly limited. For example, a method of immersing a base material having a network structure formed thereon in a washing solvent, a method of showering a base material having a network structure formed thereon in a washing solvent, and the like may be mentioned. The washing solvent is not particularly limited as long as it does not dissolve the network structure. However, water is preferred. Water is preferably RO water, pure water, ion-exchanged water, or distilled water, and more preferably RO water. The drying method after washing is not particularly limited, and conventionally known methods can be used.

EXAMPLES

The effects of the present invention will be described using the following Examples and Comparative Examples. However, the technical scope of the present invention is not intended to be limited to only the following Examples. Unless particularly stated otherwise, the operation was carried out at room temperature (25° C.). Furthermore, unless particularly stated otherwise, the units "%" and "parts" mean "% by weight" and "parts by weight", respectively.

(Production of Catheter Base Material)

Extrusion molding was performed using a polyurethane resin (manufactured by Nippon Miractran Company Limited), subsequently an annealing treatment was carried out for one hour at 100° C., and a catheter base material was produced.

(Production of Polymethoxyethyl Acrylate (PMEA))

100 g (0.77 mol) of methoxyethyl acrylate (MEA) was dissolved in 95 g of methanol, the solution was introduced into a four-necked flask and was subjected to N₂ bubbling for one hour at 50° C., and a methanol solution was prepared (methanol solution preparation step). Subsequently, an initiator solution obtained by dissolving 0.1 g of 2,2'-azobis(4-methoxy-2,4-dimethylvaleronitrile) (V-70, manufactured by Wako Pure Chemical Industries, Ltd., 10-hour half-life temperature: 30° C.) in 5 g of methanol was added to the methanol solution having MEA dissolved therein, and thereby a polymerization reaction liquid (monomer content of polymerization reaction solution: 50% by mass) was prepared. The polymerization reaction solution was polymerized, while being stirred, for 5 hours at 50° C. under a nitrogen gas atmosphere. The solution after polymerization was added dropwise to ethanol, and a polymer thus precipitated was collected. Meanwhile, the weight average molecular weight of the collected polymer (PMEA) was 400000.

The weight average molecular weight was measured by Gel Permeation Chromatography (GPC) using polystyrene as a reference material. Specifically, the polymer thus produced was dissolved in tetrahydrofuran (THF), a solution having a concentration of 1 mg/ml was prepared, and GPC of standard polystyrenes and the polymer (PMEA) was measured by attaching Shodex (registered trademark) GPC columns LF-804 (manufactured by Showa Denko K.K.) to GPC system LC-20 manufactured by SHIMADZU CORPORATION and causing THE to flow as a mobile phase. A calibration curve was produced using standard polystyrenes, and then the weight average molecular weight of the polymer was calculated.

Example 1

The PMEA (weight average molecular weight 400000) produced as described above and a cross-linked silicone produced based on Coating Agent Preparation Example 1 described in JP S61-35870 B were dissolved in ASAHIKLIN AK225 (dichloropentafluoropropane; Asahi Glass Co., Ltd.) such that the concentrations would be 0.1 v/v % and 3 v/v %, respectively, and thereby a mixed solution was produced. The catheter base material produced as described above was immersed in this mixed solution for 10 seconds using a ROBO Cylinder manufactured by IAI CORPORATION, the catheter base material was pulled up at a rate of 5 mm/sec and dried for 30 minutes at 60° C., and thereby a catheter was produced. The catheter thus produced was confirmed using a laser microscope (objective lens 150 times), and a network structure was formed on the surface.

Example 2

A silicone oil (360 Medical Fluid, Dow Corning Corp.) was dissolved in n-hexane such that the concentration would be 3 v/v %, and thereby a solution was produced. The catheter produced in Example 1 was immersed in this solution for 10 seconds using a ROBO Cylinder manufactured by IAI CORPORATION, the catheter was pulled up at a rate of 5 mm/sec and dried for 30 minutes at 60° C., and thereby a catheter with a two-layer coating, in which an upper layer (surface) containing a silicone oil and a lower layer containing a mixture of PMEA (weight average molecular weight 400000) and a cross-linked silicone, was produced. The catheter thus produced was confirmed using a laser microscope (objective lens 150 times), and a network structure was formed on the surface.

Example 3

The PMEA (weight average molecular weight 400000) produced as described above and a cross-linked silicone produced based on Coating Agent Preparation Example 1 described in JP S61-35870 B were dissolved in ASAHIKLIN AK225 (Asahi Glass Co., Ltd.) such that the concentrations would be 0.5 v/v % and 3 v/v %, respectively, and thereby a mixed solution was produced. The catheter base material produced as described above was immersed in this mixed solution for 10 seconds using a ROBO Cylinder manufactured by IAI CORPORATION, the catheter base material was pulled up at a rate of 5 mm/sec and dried for 30 minutes at 60° C., and thereby a catheter was produced. The catheter thus produced was confirmed using a laser microscope (objective lens 150 times), and a network structure was formed on the surface.

Comparative Example 1

The PMEA (weight average molecular weight 400000) produced as described above was dissolved in ASAHIKLIN AK225 (Asahi Glass Co., Ltd.) such that the concentration would be 0.1 v/v %, and thereby a solution was produced. The catheter base material produced as described above was immersed in this solution for 10 seconds using a ROBO Cylinder manufactured by IAI CORPORATION, the catheter base material was pulled up at a rate of 5 mm/sec and dried for 30 minutes at 60° C., and thereby a comparative catheter was produced. The catheter thus produced was confirmed using a laser microscope (objective lens 150 times), and the catheter had a uniform surface state.

Comparative Example 2

A cross-linked silicone produced based on Coating Agent Preparation Example 1 described in JP S61-35870 B was dissolved in ASAHIKLIN AK225 (Asahi Glass Co., Ltd.) such that the concentration would be 3 v/v %, and thereby a solution was produced. The catheter base material produced as described above was immersed in this solution for 10 seconds using a ROBO Cylinder manufactured by IAI CORPORATION, the catheter base material was pulled up at a rate of 5 mm/sec and dried for 30 minutes at 60° C., and thereby a comparative catheter was produced. The catheter thus produced was confirmed using a laser microscope (objective lens 150 times), and the catheter had a uniform surface state.

<Evaluation>

For the following evaluations, the catheter base material produced as described above was used as the comparative catheter of Comparative Example 3.

[Evaluation of Puncture Resistance]

For the catheters of Examples 1 to 3 and the comparative catheters of Comparative Examples 1 to 3, the puncture resistance (resistance to body) was measured. Specifically, an inner needle was incorporated into the catheter having an outer diameter of 0.8 mm and an inner diameter of 1.1 mm, and a polyethylene film having a thickness of 50 μm was punctured at an angle of 90 degrees at a rate of 30 mm/min using a small-sized table tester, EZ-1, manufactured by SHIMADZU CORPORATION. The maximum resistance value after passage of 10 mm from the needle tip was measured, and the value was designated as the resistance to body. In a case in which the resistance to body was 0.12 N or less, it was considered that the sliding properties were excellent. The results are presented in Table 1.

[Evaluation of Antithrombogenicity]

For the catheters of Examples 1 to 3 and the comparative catheters of Comparative Examples 1 to 3, a blood circulation experiment was carried out for 3 hours in a system as illustrated in the FIGURE. After circulation, the amount of production of a thrombin-antithrombin complex (TAT) was measured. The amount of TAT production was measured according to an EIA method. In a case in which the amount TAT production was 400 ng/ml or less, it was considered that the antithrombogenicity was excellent. The results are presented in Table 1.

TABLE 1

| | Mixed solution | | | Evaluation of antithrombogenicity | Evaluation of puncture resistance |
| | PMEA | | Cross-linked | | |
| | Concentration (v/v %) | Weight average molecular weight | silicone Concentration (v/v %) | Silicone oil* Concentration (v/v %) | Amount of TAT production (ng/mL) | Body part resistance (N) |
|---|---|---|---|---|---|---|
| Example 1 | 0.1 | 400000 | 3.0 | — | 237 | 0.1 |
| Example 2 | 0.1 | 400000 | 3.0 | 3.0 | 237 | 0.03 |
| Example 3 | 0.5 | 400000 | 3.0 | — | 350 | 0.03 |
| Comparative Example 1 | 0.1 | 400000 | — | — | 310 | 0.4 |
| Comparative Example 2 | — | — | 3.0 | — | 1170 | 0.06 |
| Comparative Example 3 | — | — | — | — | 2970 | 0.16 |

The symbol "—" in the table indicates that the substance is not incorporated.

*Solution for the production of the upper layer

As shown in Table 1, it is understood that the catheters of Examples have excellent sliding properties, specifically excellent puncture properties, and exhibit excellent antithrombogenicity, compared to the comparative catheters of Comparative Examples. Furthermore, the catheter of Example 2 coated with a two-layer coating, in which an upper layer (surface) contained a silicone oil and a lower layer contained a mixture of PMEA (weight average molecular weight 400000) and a cross-linked silicone, exhibits enhanced puncture properties (sliding properties) due to the silicone oil of the upper layer (surface) during puncture, and after puncture, the catheter can exhibit enhanced antithrombogenicity, as the silicone oil is dissolved out by the blood in the body and the mixture of PMEA (weight average molecular weight 400000) and a cross-linked silicone of the lower layer is exposed to the surface of the catheter. By having the two-layer coating, in which the upper layer (surface) containing a silicone oil and the lower layer containing a mixture of PMEA (weight average molecular weight 400000) and a cross-linked silicone, the catheter can have superior sliding properties, specifically superior puncture properties, and can exhibit excellent antithrombogenicity.

What is claimed is:

1. A medical device comprising:
a base material; and
a coating on a surface of the base material, wherein the coating comprises a network structure comprising a thread portion and a network portion; wherein:
the thread portion comprises a combination of a silicone and a compound comprising a constituent unit of polymethoxyethyl acrylate (PMEA);
and at the network portion a surface of the base material is exposed from the thread portion.

2. The medical device according to claim 1, wherein the coating comprises a cross-linked silicone.

3. The medical device according to claim 2, wherein the coating further comprises a silicone oil.

4. The medical device according to claim 3, wherein the coating has a lower layer comprising the compound and the cross-linked silicone, and an upper layer comprising the silicone oil.

5. A method for producing a medical device, the method comprising:
forming, on a surface of a base material, a coating comprising a network structure comprising a thread portion and a network portion; wherein:
the thread portion comprises a silicone and a compound comprising a constituent unit of polymethoxyethyl acrylate (PMEA);
and at the network portion a surface of the base material is exposed from the thread portion.

6. The method according to claim 5, wherein:
the step of forming the coating comprises:
immersing the surface of the base material in a mixed solution comprising a cross-linked silicone and the compound,
pulling the surface of the base material out of the mixed solution, and
drying the base material that has been pulled out of the mixed solution to form the coating on the surface of the base material.

7. A catheter comprising:
a catheter base material; and
a coating on a surface of the catheter base material, the coating comprising a network structure comprising a thread portion and a network portion; wherein:
the thread portion comprises a silicone and a compound comprising a constituent unit of polymethoxyethyl acrylate (PMEA);
and at the network portion a surface of the base material is exposed from the thread portion.

8. The catheter according to claim 7, wherein the coating comprises a cross-linked silicone.

9. The catheter according to claim 8, wherein the coating further comprises a silicone oil.

10. The catheter according to claim 9, wherein the coating has a lower layer comprising the compound and the cross-linked silicone, and an upper layer comprising the silicone oil.

11. The method according to claim 6, wherein:
the step of forming the coating further comprises:
immersing the surface of the base material, with the coating thereon, in a solution comprising a silicone oil,
pulling the surface of the base material out of the solution, and
drying the base material that has been pulled out of the solution so as to form a layered coating that has a lower layer comprising the compound and the cross-linked silicone, and an upper layer comprising the silicone oil.

* * * * *